US008580534B2

(12) United States Patent
Miyagi

(10) Patent No.: US 8,580,534 B2
(45) Date of Patent: Nov. 12, 2013

(54) METHOD FOR INCORPORATION OF TWO OXYGEN ATOMS INTO DIGESTED PEPTIDES USING PEPTIDASES

(75) Inventor: Masaru Miyagi, Shaker Heights, OH (US)

(73) Assignee: The University of North Dakota, Grand Forks, ND (US)

( * ) Notice: Subject to any disclaimer, the term of this patent is extended or adjusted under 35 U.S.C. 154(b) by 1299 days.

(21) Appl. No.: 11/824,662

(22) Filed: Jul. 2, 2007

(65) Prior Publication Data

US 2008/0032322 A1  Feb. 7, 2008

Related U.S. Application Data

(60) Provisional application No. 60/806,357, filed on Jun. 30, 2006.

(51) Int. Cl.
C12Q 1/37  (2006.01)

(52) U.S. Cl.
USPC ............................................. 435/23; 435/24

(58) Field of Classification Search
USPC ....................................................... 435/23, 24
See application file for complete search history.

(56) References Cited

U.S. PATENT DOCUMENTS

| 6,864,089 | B2 | 3/2005 | Figeys et al. |
|---|---|---|---|
| 6,908,740 | B2 | 6/2005 | Vandekerckhove et al. |
| 7,166,441 | B2 | 1/2007 | Nadler et al. |
| 7,195,751 | B2 | 3/2007 | Pappin et al. |
| 7,244,411 | B2 | 7/2007 | Núñez et al. |
| 2003/0175804 | A1 | 9/2003 | James |
| 2003/0186326 | A1 | 10/2003 | Regnier et al. |
| 2005/0032149 | A1 | 2/2005 | Yao et al. |
| 2005/0186135 | A1 | 8/2005 | Howes |
| 2006/0105415 | A1 | 5/2006 | Miyagi et al. |
| 2006/0105416 | A1 | 5/2006 | Pappin et al. |
| 2006/0263886 | A1 | 11/2006 | Peters et al. |
| 2007/0015233 | A1 | 1/2007 | Brancia |

FOREIGN PATENT DOCUMENTS

WO  WO 02/099435 A1  12/2002

OTHER PUBLICATIONS

Rao et al. "Proteolytic 18O labeling by peptidyl-Lys metal-loendopeptidase for comparative proteomics", J of Proteome Research, 2005, 4:507-514.*
Hajkova et al."pH dependency of the carboxyl oxygen exchange reaction catalyzed Lysyl endopeptidase and trypsin", J of Proteome Research, 2006, 5:1667-1673.*

D.B. Springson, et al., "Nature of the Activation Process in Enzymatic Reactions," from *Nature*, p. 484, (Mar. 24, 1951).
F. Vaslow, "Kinetics of the Chymotrypsin Catalized Oxygen Exchange of N-acetyl-3:5-dibromo-L-tyrosine," from *Biochim. et Biophys.Acta*, vol. 116, pp. 601-602 (1955).
M.L. Bender, et al., "The Kinetics of the α-Chymotrypsin-Ctalyzed Oxygen Exchange of Carboxylic Acids", from *J. Am. Chem. Soc.*, vol. 79, pp. 116-120 (Jul. 26, 1956).
S. Wang, et al., "Kinetic Studies at High pH of the Trypsin-catalyzed Hydrolysis of $N^\alpha$-Benzoyl Derivatives of $_L$-Arginamide, $_L$-Lysinamide, and S-2-Aminoethyl-$_L$-cysteinamide and Related Compounds", from *Journal of Biological Chemistry*, vol. 243, No. 13, pp. 3702-3710 (Jan. 8, 1968).
X.Yao, et al., "Dissection of Proteolytic $^{18}$O Labeling: Endoprotease-Catalyzed $^{16}$O-to-$^{18}$O Exchange of Truncated Peptide Substrates", from *Journal of Proteome Research*, pp. 147-152 (Sep. 20, 2002).
L. Zang, et al., "Protemic Analysis of Ductal Carcinoma of the Breast Using Laser Capture Microdissection, LC-MS, and $^{16}$O/$^{18}$O Isotopic Labeling", from *Journal of Proteome Research*, pp. 604-612 (Dec. 24, 2003).
A. Staes, et al., "Global Differential Non-Gel Proteomics by Quantitative and Stable Labeling of Tryptic Peptides with Oxygen-18", from *Journal of Proteome Research*, pp. 786-791 (Feb. 12, 2004).
V.K. Antonov, et al., "Studies on the Mechanisms of Action of Proteolytic Enzymes Using Heaving Oxygen Exchange," from *Eur. J. Biochem*, vol. 117, No. 1, pp. 195-200 (1981).
K.J. Reynolds, et al., "Proteolytic $^{18}$O Labeling for Comparative Proteomics: Evaluation of Endoprotease Glu-C as the Catalytic Agent," from *Journal of Proteome Research*, vol. 1, No. 1, pp. 27-33 (Jan. 2002).
M. Heller, et al., "Trypsin Catalyzed $^{16}$O-to-$^{18}$O Exchange for Comparative Proteomics: Tandem Mass Spectrometry Comparison Using MALDI-TOF, ESI-QTOF, and ESI-Ion Trap Mass Spectrometers," from *Journal of the American Society for Mass Spectrometry*, vol. 14, No. 7, pp. 704-718 (Jul. 2003).

* cited by examiner

*Primary Examiner* — Bin Shen
(74) *Attorney, Agent, or Firm* — Kinney & Lange, P.A.

(57) ABSTRACT

A method for comparative proteomics using a peptidase under enzymatic conditions that permits the optimal incorporation of two oxygen atoms into a digested peptide. The method employs a peptidase to incorporate two $^{18}$O atoms into a peptide set derived from a population of proteins at a conditioned state, which is compared to a second peptide set incorporated with a single $^{16}$O atom derived from a population of proteins at a second conditioned state. Upon combining the two peptide sets, the populations of proteins are analyzed for qualitative and quantitative differences based on the content of $^{18}$O atoms and $^{16}$O atoms in the digested peptides using mass spectrometry instrumentation. The method is advantageous to improve the efficiency and timeframe of peptidase catalyzed $^{18}$O labeling reactions which increased the accuracy and reliability of quantitative proteomic experiments.

25 Claims, 5 Drawing Sheets

METHOD FOR INCORPORATION OF TWO OXYGEN ATOMS INTO DIGESTED PEPTIDES USING PEPTIDASES

REFERENCE TO COPENDING APPLICATION

This application claims priority from Provisional Application No. 60/806,357 filed Jun. 30, 2006, which is incorporated by reference.

STATEMENT OF GOVERNMENT INTEREST

This invention was made with government support under Grant Nos. R03EY014020. P20RR016741, and P20RR017699 awarded by the United States Department of Health and Human Services (National Institutes of Health). The government has certain rights in the invention.

BACKGROUND

The completion of the genome sequencing of humans and other species and the emergence of new technologies in mass spectrometry has together fostered unprecedented opportunities for studying proteins on a large scale. It is expected that large scale quantitative measurements of protein expression in different sets of samples, referred to as comparative proteomics, will advance our understanding of physiological processes and disease mechanisms. Comparative proteomic approaches have been applied to various biological samples to identify and quantify proteins that are up- or down-regulated in response to biological conditions. To date, there are two primary strategies used in current comparative proteomics; two dimensional gel electrophoresis (2D-PAGE) based strategy and mass spectrometry based in vitro stable isotope labeling strategy.

Although 2D-PAGE based methods have been a primary choice in comparative proteomics, 2D-gels are cumbersome to run, have a poor dynamic range, and are biased toward abundant and soluble proteins. In contrast, the mass spectrometry based stable isotope labeling strategy has a potential of overcoming most of the weaknesses of the 2D-PAGE based methods. If the stable isotope labeling can be achieved efficiently and equivalently for each distinct sample, then two samples may be compared using isotopic ratios. Among the in vitro stable isotope labeling methods, proteolytic $^{18}O$ labeling is the simplest stable isotope labeling method and is expected to have the least methodological error (technical variations). Therefore, the proteolytic $^{18}O$ labeling method has the potential to be a central method in comparative proteomics.

Currently, there are two ways to incorporate stable isotopes into peptides; first by derivatization of peptides by a light- or heavy-isotope coded reagent (Isotope Coded Affinity Tag or ICAT), or second by incorporation of $^{16}O$ and $^{18}O$ atom(s) into the carboxyl termini of peptides from the solvent water, $H_2^{16}O$ or $H_2^{18}O$, respectively, upon proteolytic cleavage of proteins. The second method is referred to as a proteolytic $^{18}O$ labeling method where a peptidase is used.

Although promising, a major drawback of the proteolytic $^{18}O$ labeling method has been the generation of a mixture of isotopic isoforms upon proteolytic digestion resulting from the differential incorporation of either one or two $^{18}O$ atoms ($^{18}O_1/^{18}O_2$) into each digested peptide species generated. Typically the serine proteases used include trypsin, Lys-C or Glu-C proteases. Unfortunately, past studies have found that the ratios of the first and the second $^{18}O$ atom incorporation vary significantly with peptide sequences, and thus, the ratios of $^{18}O_1$- and $^{18}O_2$-peptides cannot be predicted with any certainty. The quantifications of the peptides results in significant errors in the calculations of $^{16}O$- and $^{18}O$-labeled peptide ratios. In spite of a more recent appreciation of this problem, no method has been reported to solve the problem.

Hydrolysis of a protein in $H_2^{18}O$ solvent by serine proteases may result in the incorporation of two $^{18}O$ atoms into the carboxyl terminus of each proteolytically generated peptide provided that a sufficiently long time was given for the reaction to reach equilibrium. Studies done by Yao et al. demonstrated that the two $^{18}O$ atoms are incorporated by trypsin at equilibrium via the following two step mechanism:

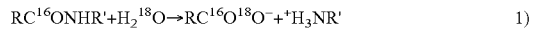

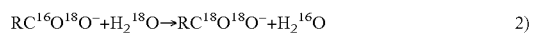

The first $^{18}O$ atom is incorporated from the $H_2^{18}O$ solvent upon proteolytic cleavage of a peptide bond, as shown in reaction 1. The second $^{18}O$ atom incorporation is essentially a carboxyl oxygen exchange reaction as shown in reaction 2, which occurs subsequent to proteolytic cleavage. The protease continues to interact with the peptide product and exchange the carboxyl oxygen, which results in two $^{18}O$ atoms incorporation, if the first $^{18}O$ atom is retained. However, reaction 2 is required to occur numerous times on the peptide to achieve complete incorporation of two $^{18}O$ atoms. If the reaction continues, both oxygen atoms in the C-terminal carboxyl group of the peptide should theoretically come to equilibrium with oxygen from the $H_2^{18}O$ solvent. However, the reaction time required has proven to be not feasible and far less predictable than necessary to be utilized in labeling peptides for proteomics analysis.

In a recent invention (U.S. Patent Publication No. 2006/0105415) we reported that the incorporation of a single $^{18}O$ atom can be accomplished using $H_2^{18}O$ solvent under conditions that optimize labeling based on reaction 1 upon proteolytic cleavage of a peptide bond while eliminating the slower rate limiting reaction 2. We demonstrated that at a higher pH reaction 1 could be optimized for incorporation of a single $^{18}O$ atom upon protease cleavage and essentially no incorporation of a second $^{18}O$ atom occurred. The conditions for various suitable proteases can be optimized to facilitate incorporation of a single $^{18}O$ atom, avoid eliminating drawbacks previously employed for $^{18}O$ labeling with peptidases, and provide highly accurate quantification method for comparative proteomics.

Complete double $^{18}O$ atom incorporation has been more problematic to resolve because of the carboxyl oxygen exchange reaction. The carboxyl oxygen exchange reaction was found by Rittenberg and Sprinson for chymotrypsin fifty years ago. Shortly after their finding, Doherty and Vaslow demonstrated by an enzyme-substrate equilibrium experiment that the binding of acetyl-3,5-dibromo-L-tyrosine to chymotrypsin is stronger at acidic pH than alkaline pH. The kinetic parameters of chymotrypsin-catalyzed carboxyl oxygen exchange reaction have also been reported by Vaslow for acetyl-3,5-dibromo-L-tyrosine at pH 7.2 and by Bender and Kemp for benzoyl-L-phenylalanine and acetyl-L-tryptophane at pH 7.8. Recently, Yao and coworkers have reported kinetic parameters of trypsin-catalyzed carboxyl oxygen exchange reaction at pH 8.0 for short peptide substrates. However, low pH studies were not performed in these kinetic studies. A recent study done by Zang and coworkers showed that a trypsin-catalyzed carboxyl oxygen exchange reaction at pH 6.75 is more efficient than at pH 8.50 based on an experiment that measured the changes of isotopic peaks of the labeled peptides after 20 hours of labeling reactions. More recently, a study performed by Staes and coworkers in a lengthy three step process consisting of digestion with trypsin overnight, inactivation of trypsin by reductive alkylation, and finally overnight incubation at pH 4.5 with two $^{18}$O atoms reported that incorporation of two $^{18}$O atoms was achieved. However, these earlier works did not measure reaction rates or pH optima, therefore no quantitative information or optimal kinetic parameters on the rate of the reaction were obtained.

SUMMARY

The present invention has found that under unique conditions peptidases are able to preferentially incorporate two $^{18}$O atoms into each digested peptide at a determined optimal pH for the reaction. The described invention resolves previous commercial problems in utilizing proteases by using a rapid, simplified method in conjunction with $^{18}$O-labeled peptides to accurately quantify different protein populations. The described invention provides for broad application for proteases by optimizing enhanced incorporation of two $^{18}$O atoms into peptides to provide for a highly accurate quantification method for comparative proteomics.

The present invention is a method for incorporation of two oxygen atoms into a digested peptide using a peptidase. A protein or set of proteins is treated with a peptidase under optimized conditions that facilitate incorporation of two oxygen atoms in the carboxyl terminus of the digested peptide. The present invention is further directed to the mass spectrometry comparison of protein expression in different biological conditions using a peptidase to incorporate two $^{18}$O oxygen atoms into a peptide set derived from a population of proteins at a conditioned state which is compared to a second peptide set, derived from a population of proteins at a second conditioned state, in which two $^{16}$O oxygen atoms are incorporated.

The invention includes a method for incorporating two oxygen atoms into a digested peptide. A solution of peptidase and water is formed and a protein is digested with the solution. The solution may also contain buffer to provide and maintain a pH that favors the digestion reaction. An additional solution of peptidase and $H_2^{18}O$ water is formed and the digested proteins are incubated with the second solution. The second solution may also contain buffer to provide and maintain a pH that favors the carboxyl oxygen exchange reaction. The incubation occurs at an optimal pH that is within 1 pH unit of the pH where the carboxyl oxygen exchange reaction has its highest initial velocity. During the incubation step, the two oxygen atoms on the carboxyl termini of the digested peptides are exchanged with the $^{18}$O from the $H_2^{18}O$ water and, thus two $^{18}$O are incorporated into the digested peptide.

The invention also includes another method for incorporating two oxygen atoms into a digested peptide. A solution of peptidase and $H_2^{18}O$ water is formed. The solution may also contain buffer to provide and maintain a pH that is within 1 pH unit of a pH where the initial velocities of both the amide hydrolysis reaction and the carboxyl oxygen exchange reaction are equal. Digestion of the protein and incubation of the digested peptides both occur contemporaneously in the presence of the solution. During digestion and incubation, oxygen atoms on the carboxyl termini of the peptides are exchanged via hydrolysis or the carboxyl oxygen exchange reaction. Two oxygen atoms on the carboxyl termini of the digested peptides are exchanged with the $^{18}$O from the $H_2^{18}O$ water and, thus two $^{18}$O are incorporated into the digested peptide.

The invention further includes a method for comparative proteomics. Mass spectrometry is used to compare proteins of different biological conditions. A protein of first biological condition is digested and also incubated with peptidase and $H_2^{18}O$ to facilitate the incorporation of two $^{18}$O atoms into the digested peptide. A protein of second biological condition is digested and also incubated with peptidase and $H_2^{16}O$ to facilitate the incorporation of two $^{16}$O atoms into the digested peptide. The digested peptides of both first and second biological condition are then mixed and mass spectrometry is used to analyze the relative ratios of $^{18}$O and $^{16}$O in the mixed digested peptides.

The invention further comprises a kit for incorporating two oxygen atoms into a digested peptide. The kit comprises peptidase and $H_2^{18}O$ water. The kit may also include buffer to provide an optimal pH that is within 1 pH unit of the pH where the carboxyl oxygen exchange reaction has its highest initial velocity or within 1 pH unit of a pH where the initial velocities of both the amide hydrolysis reaction and the carboxyl oxygen exchange reaction are equal.

DETAILED DESCRIPTION

Figure 1:
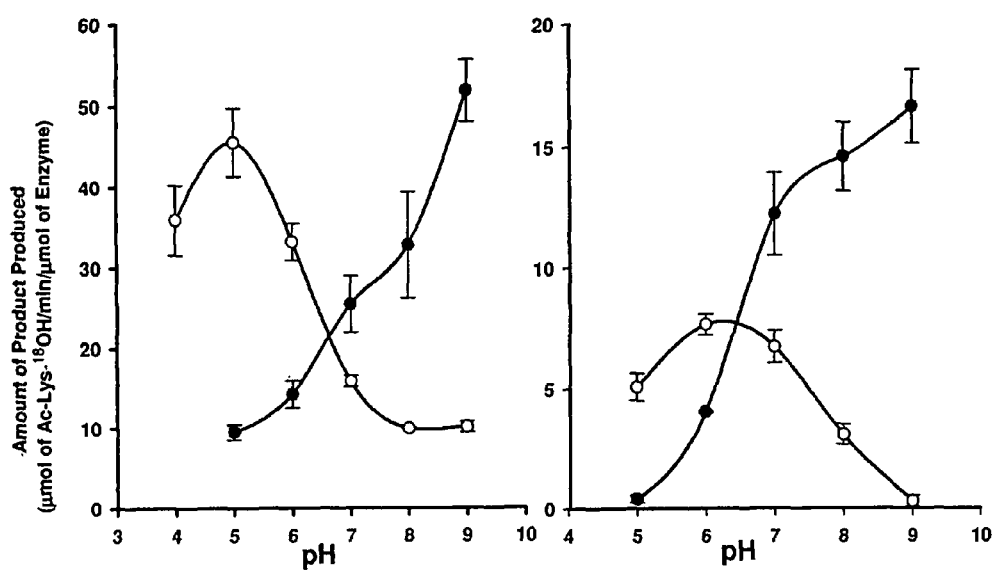
FIG. 1 shows the effects of pH on the initial velocities of the carboxyl oxygen exchange (○) and amidase (●) activities of Lys-C (left panel) and trypsin (right panel).

"Biological condition" means any physiological or cellular condition of a plant, animal, microorganism, organ, cell or other biological material.

"pH optimized conditions" means any conditions and its components that are pH optimized for the incorporation of two oxygen atoms into a digested peptide using a peptidase. The pH is optimized for conditions that include, but are not limited to, increased carboxyl oxygen exchange activity and decreased amidase activity.

"Two oxygen atom" means at least a 90% incorporation of two oxygen atoms, and more preferably, 95%, 98% or greater incorporation of two oxygen atoms into the digested peptide. Examples of oxygen atoms include, but are not limited to, $^{16}$O atoms and $^{18}$O atoms.

"Stable oxygen isotope" means any stable isotope of oxygen such as $^{16}$O and $^{18}$O.

"$^{18}$O enriched water" means water containing at least 90% $^{18}$O atom, and more preferably, 95%, 98% or greater, where $^{16}$O oxygen atoms comprise the remainder of the oxygen atoms in water.

"$^{16}$O water" means all naturally occurring water.

Traditionally mass spectrometry based comparative proteomic methods are based on in vitro labeling of two stable isotopes. For example, the peptides from the control sample are labeled with naturally abundant (light) isotope(s), while peptides from the experimental sample are labeled with its heavier isotope(s) or vice versa. The samples are then mixed together in equal proportion and analyzed by mass spectrometry. Since a peptide labeled with the light isotope and the same peptide labeled with the heavier isotope give different molecular weights, the light- and heavy-peptide can be distinguished by mass spectrometry. By comparing the peak areas or intensities of the light-peptide and heavy-peptide, the relative abundance of the two peptides can be determined. These ratios can further be used to quantify the relative abundance of each parent protein in the distinct original samples.

As a further illustration of the commercial application using this comparative approach, a pool of isotopically labeled proteins acquired from an unstressed system is mixed with the same relative amount of an unlabeled sample from a second (stressed) experimental system or vice visa. The combined pool is then analyzed by mass spectrometry to rapidly determine the stressed proteins relative to the unstressed state. The applications of this method would be highly useful to identify and quantify changes in protein expression in a variety of diseased or physiological states in animals, plants and microorganisms.

There has been an increasing interest in the use of protease catalyzed $^{18}O$ labeling for quantitative proteomics. However, this method often suffers because of the generation of a mixture of isotopic isoforms resulting from the variable incorporation of either one or two $^{18}O$ atoms ($^{18}O_1/^{18}O_2$) into each peptide species, presumably because the second $^{18}O$ atom incorporation reaction (carboxyl oxygen exchange reaction) is extremely slow under the conditions commonly used for protein digestion, leading to incomplete and variable exchange in the time frame of the proteolytic reaction. This complicates the quantification of the peptides and increases the error in the calculations of $^{16}O$ and $^{18}O$-labeled peptide ratios. Complete incorporation of two $^{18}O$ atoms would obviate this difficulty and reduce the qualitative and quantitative errors introduced by partial incorporation of $^{18}O$ atoms. A near complete incorporation of two $^{18}O$ atoms to achieve this would be a significant step towards improving quantitative proteomics methods utilizing $^{18}O$ labeling.

The purpose of this invention is to determine optimized conditions for the catalytic mechanism of carboxyl oxygen exchange reaction promoted by serine proteases. Lys-C and trypsin were chosen, because they have been the most utilized proteases in $^{18}O$ labeling experiments. Since the substrate for carboxyl oxygen exchange reaction (RCOO—) has a negative charge at the C-terminus at physiological pH, while the corresponding substrate for amide hydrolysis reaction (RCONH$_2$) does not, it seems reasonable to assume that the mechanism of enzyme-substrate complex formation in the carboxyl oxygen exchange reaction is somewhat different from the mechanism in the amide bond hydrolysis reaction. For this reason, the pH dependency of the carboxyl oxygen exchange reaction for N-acetyl-L-lysine (Ac-Lys-OH) catalyzed by Lys-C and trypsin was examined, utilizing H$_2$$^{18}$O as a carboxyl oxygen labeling agent. The single $^{18}O$ atom incorporated reaction product, Ac-Lys-$^{18}$OH, was quantified by stable isotope dilution tandem mass spectrometry. Steady state kinetics parameters for the carboxyl oxygen exchange reaction were also obtained. Based on these results, conditions for use of Lys-C and trypsin to efficiently incorporate two $^{18}O$ atoms into the carboxyl termini of peptides are suggested.

The members of the peptidase family are any enzymes that hydrolyze peptide bonds (EC 3.4, Enzyme Nomenclature 1992, Academic Press, San Diego, Calif.). Peptidases are present in a wide variety of biological sources and contain the amino acid sequence motif comprising His-Glu-Xaa-Xaa-His, where Xaa is any amino acid. The peptidase family can be subdivided into exopeptidases (EC 3.4.11-19) and endopeptidases (EC 3.4.21-99), the latter referred to as proteinases, that act near the terminus of the polypeptide or internally, respectively. Subclasses of exopeptidases include those acting at a free N-terminus releasing a single amino acid (aminopeptidase, EC 3.4.11), a dipeptide (dipeptidyl-peptidase, EC 3.4.14), or a tripeptide (tripeptidyl-peptidase, EC 3.4.14) and those at a free C-terminus releasing a single amino acid (carboxypeptidase, EC 3.4.16-18) or a dipeptide (peptidyl-dipeptidase, EC 3.4.15). Other exopeptidases are specific for dipeptides (dipeptidases, EC 3.4.13) or remove terminal residues that are substituted, cyclized or linked by isopeptide bonds (omega peptidases, EC 3.4.19). Subclasses of endopeptidases (EC 3.4.21-24 and EC 3.4.99) are subdivided on the basis of catalytic mechanism and specificity is used only to identify individual enzymes within the groups. Subclasses of serine endopeptidases (EC 3.4.21), cysteine endopeptidases (EC 3.4.22), aspartic endopeptidases (EC 3.4.23), metalloendopeptidases (EC 3.4.24) and threonine endopeptidases (EC 3.4.25). Endopeptidases that cannot be assigned to any of the sub-subclasses EC 3.4.21-25 are listed in sub-subclass EC 3.4.99.

In the present invention it is demonstrated that the rate of carboxyl oxygen exchange reaction by Lys-C and trypsin can be accelerated significantly by carrying out the labeling reaction at acidic pH conditions used in the present work. The catalytic activities (kcat/KM) of Lys-C and trypsin at acidic pHs were 2.5-fold and 17-fold higher than those at alkaline pHs, respectively. This finding is significant towards improving the accuracy of $^{18}O$ labeling in quantitative proteomic experiments by identifying the conditions that lead to the complete incorporation of two $^{18}O$ atoms into peptides. This study supports the use of separate experiments for digestion of proteins and $^{18}O$ labeling of the generated peptides, as each can be optimized separately (the digestion at pH 8, and the labeling at pH 5-6). Endoproteinase Glu-C and chymotrypsin have also been shown to be effective catalysts to incorporate two $^{18}O$ atoms into peptides.

It was found that the activity of carboxyl oxygen exchange reaction of Lys-C (kcat/Km) at pH 5.0 was 17-fold higher than that of trypsin at pH 6.0 when Ac-Lys-OH was used as a substrate. The amidase activities of Lys-C for N-benzoyl-L-lysine amide and N$^\alpha$-benzoyl-lysine-p-nitroanilide have been reported to be an order of magnitude higher than that of trypsin. Thus, it is apparent that the use of Lys-C as a catalyst in $^{18}O$ labeling experiment has an advantage over trypsin in terms of efficiency of $^{18}O$ labeling in both the first and the second $^{18}O$ atom incorporation (reaction 1 and 2, respectively, in Background). However, Lys-C produces peptides that are larger compared to peptides produced by trypsin, therefore a high resolution mass spectrometer may be required for the analysis of the peptides because of the tendency of larger peptides to produce higher charge states than smaller peptides when electrospray is used.

EXAMPLE 1 pH Dependency of the Carboxyl Oxygen Exchange Reaction for Ac-Lys-OH

N-acetyl-L-lysine (Ac-Lys-OH), N-acetyl-L-lysine amide (Ac-Lys-NH$_2$) and N-tert-butyloxycarbonyl-L-lysine (H-Lys (Boc)-OH) were purchased from Bachem AG (Torrance, Calif.). Horse apomyoglobin and [$^{13}C_4$] acetic anhydride were obtained from Sigma-Aldrich (St. Louis, Mo.). Oxygen-18 enriched water (>95%) was obtained from Cambridge Isotope Laboratories (Andover, Mass.). Lys-C from Achromobacter lyticus was purchased from Wako Chemicals USA (Richmond, Va.). Sequencing grade modified porcine trypsin was obtained from Promega (Madison, Wis.). All other chemicals and materials were either reagent grade or were of the highest quality that was commercially available.

N-[$^{13}C_2$]acetyl-lysine ([$^{13}C_2$]Ac-Lys-OH) was synthesized by acetylating H-Lys(Boc)-OH (50 mM) by [$^{13}C_4$] acetic anhydride (2 mM) for 16 hours at 25° C. in 0.8 mM N-ethylmorpholine, 50% acetonitrile in water. After the reaction, the reaction mixture was dried in a speed-vac, and then the Boc group was cleaved by 3 M HCl in ethyl acetate for 30 minutes at 25° C. The product, [$^{13}C_2$]Ac-Lys-OH, was extracted in water and purified by reverse phase HPLC. The molecular weight of the purified [$^{13}C_2$]Ac-Lys-OH was determined by high resolution mass spectrometry [$^{13}C_2C_6H_{17}N_2O_3$] (M+H$^+$): calculated, 191.1306; found, 191.1261]. [$^{13}C_2$]Ac-Lys-OH in water was quantified by spectrophotometry at 215 nm using a molar absorption coefficient for Ac-Lys-OH of 877 M$^{-1}$·cm$^{-1}$ and was used for the following experiments.

The initial rate of carboxyl oxygen exchange reaction catalyzed by Lys-C and trypsin was determined by monitoring the rate of $^{18}O$ atom incorporation into the carboxyl terminus of Ac-Lys-OH. For the pH studies, a 10 mM solution of Ac-Lys-OH in aqueous buffers at different pHs was incubated with 1 µM Lys-C or trypsin at 25° C. in 95% H$_2^{18}$O buffered at various pHs. The buffer solutions used were 50 mM citrate at pH 4.0, 5.0 and 6.0 (pH adjusted by addition of NaOH), 50 mM phosphate at pH 7.0 and 8.0 (pH adjusted by addition of NaOH) and 50 mM Tris at pH 9.0 (pH adjusted by addition of HCl). The duration of the reaction was 5 minutes for Lys-C and 20 minutes for trypsin. All the reactions were confirmed to be linear within the time range. The total volume of the reaction mixture was 50 µL. The reaction was stopped by adding 4-times the volume of 80% acetonitrile/1% formic acid (v/v) in water containing a constant amount of internal standard, [$^{13}C_2$]Ac-Lys-OH (0.75 µg), dried in a speed-vac concentrator, and redissolved in 50 uL of 5% acetonitrile/ 0.1% heptafluorobutyric acid (HFBA) (v/v) in water. The single $^{18}O$ atom incorporated reaction product, Ac-Lys-$^{18}$OH, in the reconstituted reaction solution was then quantified by stable isotope dilution tandem mass spectrometry, as described below. All reactions were carried out in triplicate.

The amidase activity of Lys-C and trypsin was measured by monitoring the initial rate of hydrolysis of Ac-Lys-NH$_2$ in H$_2^{18}$O. Ac-Lys-NH$_2$ (10 mM) was incubated with 0.2 uM Lys-C or 1 uM trypsin at 25° C. in 95% H$_2^{18}$O at various pHs. The buffer solutions used were the same as described above for the carboxyl oxygen exchange reactions. The duration of the reaction was 5 min for Lys-C and 20 min for trypsin. The single $^{18}O$ atom incorporated reaction product, Ac-Lys-$^{18}$OH, was quantified after addition of a [$^{13}C_2$]Ac-Lys-OH internal standard (0.75 µg) by stable isotope dilution tandem mass spectrometry, as described below. All reactions were carried out in triplicate.

The pH dependency of the carboxyl oxygen exchange reaction measured by the incorporation of an $^{18}O$ atom into Ac-Lys-OH catalyzed by Lys-C and trypsin is shown in FIGS. 1a and b, respectively. The pH dependency of amidase activities obtained for the Ac-Lys-NH$_2$ are also shown in the figure. The optimum pHs of the carboxyl oxygen exchange reaction catalyzed by Lys-C and trypsin were found to be pH 5.0 and 6.0, respectively, which were 3-4 pH units lower than the most favorable pHs for the amidase activities (pH 9) within the pH range examined.

EXAMPLE 2

Measurement of the Steady-State Kinetic Parameters for the Carboxyl Oxygen Exchange Reaction The steady-state kinetic parameters for the carboxyl oxygen exchange reaction by Lys-C and trypsin were obtained at two different pHs (pH 9.0 and 5.0 for Lys-C and pH 8.0 and 6.0 for trypsin). Ac-Lys-OH (0.0625-10 mM) was incubated with 1 uM Lys-C or trypsin at 30° C. in 95% H$_2^{18}$O buffered at various pHs (described above). The total volume of the reaction was 20 µL. The duration of the reaction was 10 min for Lys-C and 20 min for trypsin. The single $^{18}O$ atom incorporated reaction product, Ac-Lys-18OH, was quantified after addition of a [$^{13}C_2$]Ac-Lys-OH internal standard (0.75 µg) by stable isotope dilution tandem mass spectrometry, as described below. All reactions were carried out in triplicate.

Km and V$_{max}$ values were calculated by fitting the Michaelis-Menten equation to the experimental data using Sigma-Plot 9.01 (Systat Software, Richmond, Calif.). Kcat values were calculated by dividing the obtained V$_{max}$ values by the total enzyme amount added to the system.

Figure 2:
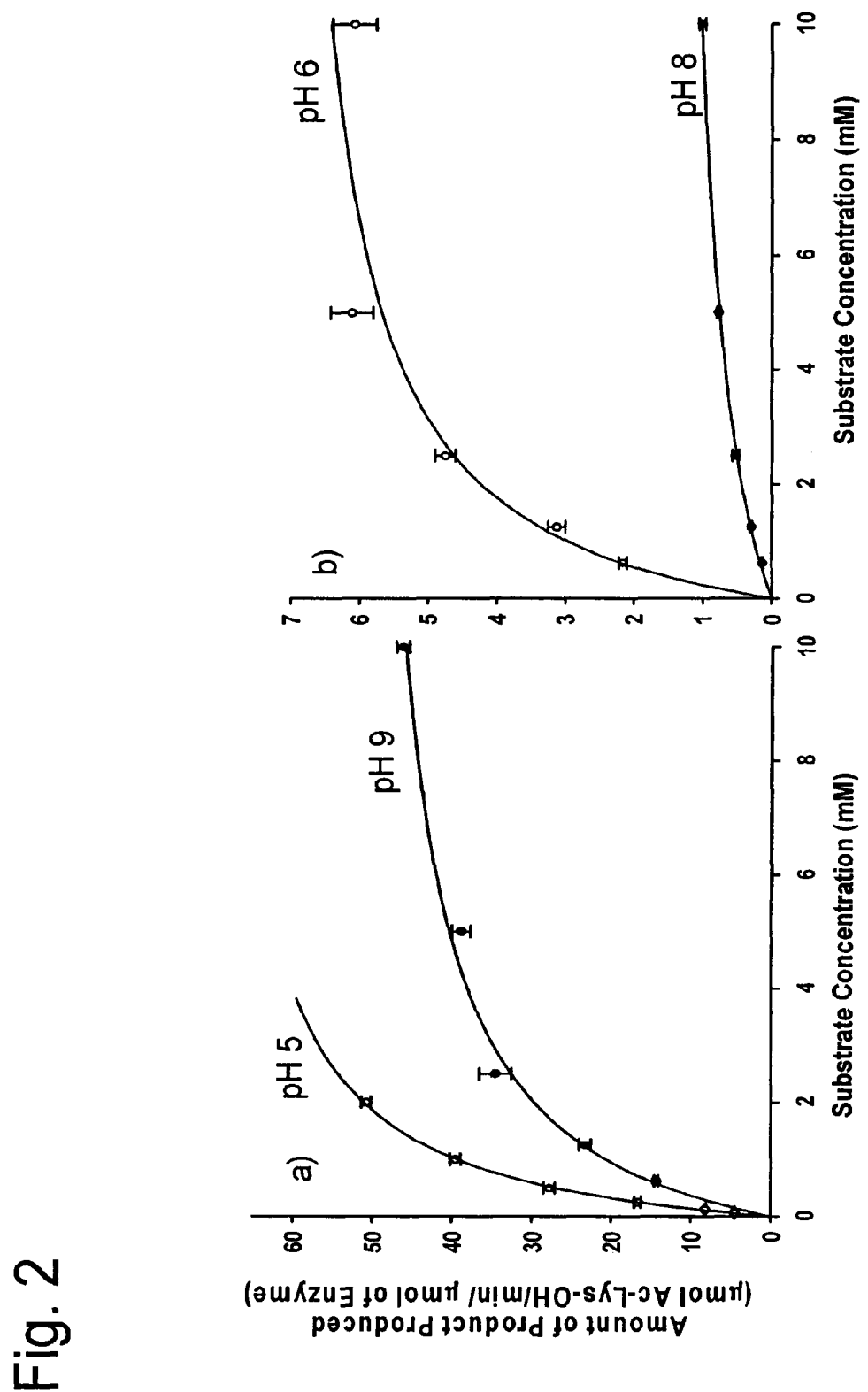
FIG. 2 shows the effects of substrate concentration at acidic and basic pH on the initial velocity of the carboxyl oxygen exchange reaction for Lys-C (left panel) and trypsin (right panel).

The reactions were performed at the acidic and alkaline pH optimums of the carboxyl oxygen exchange and amidase reactions, respectively. FIG. 2a shows the effects of substrate concentration on the initial velocity of the carboxyl oxygen exchange reaction catalyzed by Lys-C at pH 5.0 and 9.0. Similarly, FIG. 2b shows the effects of substrate concentration on the initial velocity of the carboxyl oxygen exchange reaction catalyzed by trypsin at pH 6.0 and 8.0. From the plots in FIGS. 2a and 2b, it is noticeable that the Km values decrease and the V$_{max}$ values increase with a decrease in pH. Note that the high pH trypsin catalyzed reaction was done at pH 8.0, because the rate of the carboxyl oxygen exchange was too low at pH 9.0 (most favorable pH for the amidase activity in the pHs examined) to accurately measure the kinetic parameters.

The Km and kcat values were calculated by fitting the Michaelis-Menten equation to the experimental data for the two enzymes at acidic and alkaline pHs. For Lys-C at pH 5.0, the Km was about 2-fold smaller, the kcat was about 1.5-fold higher, and the kcat/Km was about 2.5-fold higher than the Km, kcat, and kcat/Km, respectively, at pH 9.0. For trypsin at pH 6.0, the Km was about 3-fold smaller, the kcat was about 5-fold higher, and the kcat/Km was about 17-fold higher than the Km, kcat, and kcat/Km, respectively, at pH 8.0. These results show that Lys-C and trypsin have higher substrate binding affinities and higher catalytic rates at the acidic pHs. The higher substrate binding affinities of Lys-C and trypsin to the substrate for carboxyl oxygen exchange reaction at the acidic pHs are consistent with the result obtained for chymotrypsin by others; therefore, this enzymatic property may be a common feature of serine proteases.

The experimentally determined kcat/Km value for carboxyl oxygen exchange reaction by Lys-C at pH 5.0 was 1.42 mM$^-$·s$^{-1}$, which is only 3.4-fold lower than the reported kcat/Km value for amide hydrolysis of N'-benzoyl-L-lysine amide at pH 8.5 (4.81 mM$^-$·s$^{-1}$; Masaki, T., Soejima, M., Tanpakushitsu Kakusan Koso 1984, 29, 1532-1537), suggesting that the carboxyl oxygen exchange catalytic activity of Lys-C at the acidic pH is almost equivalent with its amidase activity at alkaline pH. Similarly, for trypsin at pH 6.0, the experimentally determined kcat/Km value for carboxyl oxygen exchange reaction was 0.083 mM$^-$·s$^{-1}$, which is 5.1-fold lower than the reported kcat/Km value for amide hydrolysis of N-benzoyl-L-lysine amide at pH 8.0 (0.41 mM$^-$·s$^{-1}$; Wang, S. S., Carpenter, F. H., J. Biol. Chem. 1968, 243, 3702-3710). Also, the difference of both values is less than an order of magnitude.

The higher value of kcat/Km for Lys-C at pH 5.0 compared to the value at pH 9.0 is due mainly to the effect of the decreased value of the Km component on the ratio, while both the Km and kcat significantly contribute to the higher kcat/Km of trypsin at the acidic pH. The results suggest that Lys-C catalyzes the reaction more efficiently than trypsin at alkaline pH by an as yet unknown mechanism.

EXAMPLE 3

Quantification of Ac-Lys-$^{18}$OH by Stable Isotope Dilution Tandem Mass Spectrometry An Agilent 1100 HPLC system (Palo Alto, Calif.) coupled to an API 3000 triple quadrupole mass spectrometer equipped with a TurboIonSpray™ ion source (Applied Biosystems-MDS-Sciex, Foster City, Calif.) was used to quantify Ac-Lys-$^{18}$OH. The reconstituted reaction mixtures were injected (typically 5 µL) onto a reversed-phase C18 column (2.1×150 mm, 5 µm, 300 Å, Vydac) equilibrated with 5% acetonitrile/ 0.1% HFBA (v/v) in water and then eluted with the same solvent at a flow rate of 200 µL/min. A switching valve (Valco Instrument, Houston, Tex.) was placed between the HPLC system and the mass spectrometer to divert non-volatile salt fractions from the mass spectrometer at the beginning of the run. The switching valve was switched in-line with the mass spectrometer at 3 minutes after the injection. The elution time of Ac-Lys-$^{18}$OH was 3.8 minutes.

The ion spray voltage and the ion source probe temperature were set at 5 kV and 400° C., respectively. Nitrogen was used both as a nebulizer and as an auxiliary gas, at flow rates of 3 and 8 L/min, respectively. A multiple reaction monitoring mode was used for monitoring Ac-Lys-$^{18}$OH and [$^{13}C_2$]Ac-Lys-OH. The precursor and fragment ions monitored were m/z 191 (Ac-Lys-$^{18}$OH+H) and 149 (H-Lys-$^{18}$OH+H) for Ac-Lys-$^{18}$OH and m/z 191 ([$^{13}C_2$]Ac-Lys-OH+H) and 147 (H-Lys-$^{16}$OH+H) for [$^{13}C_2$]Ac-Lys-OH, respectively. The collision energy was 20 eV for both the analyte and internal standard. Nitrogen was used as the collision gas.

Amounts of Ac-Lys-$^{18}$OH in the reaction mixture were determined from the chromatographic peak area ratios of the analyte over the internal standard, assuming identical ionization efficiencies and identical yields of fragment ions for Ac-Lys-$^{18}$OH and [$^{13}C_2$]Ac-Lys-OH. The experimentally determined amounts of Ac-Lys-$^{18}$OH were corrected upward 5%, accounting for 60 incorporation resulting from the $H_2^{18}O$ solvent having a 5% $H_2^{16}O$ content. The assay method showed good linearity over the concentration range of 1.95-1,000 µM ($r^2>0.999$). A S/N=20 was obtained for 1.95 µM Ac-Lys-OH.

EXAMPLE 4

Measurement of the Carboxyl Oxygen Exchange Reaction for Lys-C and Tryptic Peptides of Apomyoglobin We semi-quantitatively measured the rate of $^{18}$O atom incorporation into Lys-C and tryptic peptides derived from apomyoglobin. This was done to test whether the increased rate of carboxyl oxygen exchange noted for the reaction of Ac-Lys-OH at acidic pH could be generalized to peptide substrates. Apomyoglobin (34 µg) was digested for 16 hours at 25° C. with either 1 µg of Lys-C or trypsin in 100 mM ammonium bicarbonate in $H_2^{16}O$ solvent. The digestion was stopped by adding formic acid to a final concentration of 1% and by boiling the reaction mixture for 2 minutes. The resulting Lys-C and tryptic peptides were lyophilized and used in the following experiments.

The rate of the carboxyl oxygen exchange reaction into the Lys-C and tryptic peptides by Lys-C and trypsin, respectively, were semi-quantitatively measured by looking at the rate of $^{18}$O atom incorporation into the carboxyl termini of the peptides by LC/MS (described below). The Lys-C and tryptic digests (both 1.5 µg) were incubated with Lys-C and trypsin (both 0.03 µg), respectively, in $H_2^{18}O$ at 30° C. buffered (see above) at pH 5.0 or 9.0 for Lys-C and pH 6.0 or 8.0 for trypsin for various reaction times (1 minute-60 minutes). The total reaction volume was 50 µL. Aliquots (5 µL) of the reaction mixtures were taken after 1, 5, 10, and 60 minutes. The reactions were stopped by mixing with 40 µL of 10% formic acid and by heating at 95° C. for 2 minutes. After the heat treatment, the solvents were evaporated in the speed-vac concentrator and the samples were stored at –20° C. until use.

The stored $^{18}$O labeled peptide mixtures were reconstituted in 20 µL of aqueous 0.1% trifluoroacetic acid (TFA), desalted by a C18 ZipTip as per the manufacturer's instructions (Millipore, Bedford, Mass.), and subjected to LC/MS analysis using an UltiMate nano HPLC system (Dionex, San Francisco, Calif.) interfaced to a QStar quadrupole/time of flight mass spectrometer (Applied Biosystems-MDS Sciex, Foster City, Calif.), as described previously. Briefly, the peptide mixture (5 µl) was injected directly into a reverse-phase analytical column (0.075×60 mm, New Objective Inc., Woburn, Mass.) packed with Jupiter C18 media (Phenomenex, Torrance, Calif.), washed with 2% acetonitrile/0.1% formic acid (v/v) in water for 15 minutes at flow rate of 2 µL/min. The peptides were then eluted with a 40 minute linear gradient of 2% acetonitrile/0.1% formic acid (v/v) in water to 40% acetonitrile/0.1% formic acid (v/v) in water at a flow rate of 200 nL/min. The column effluent was directed on-line to a nano-electrospray ion source. The total ion current was obtained in the mass range of m/z 400-1600 in the positive ion mode. The electrospray and orifice voltages were 2050V and 65V, respectively.

Figure 3A:
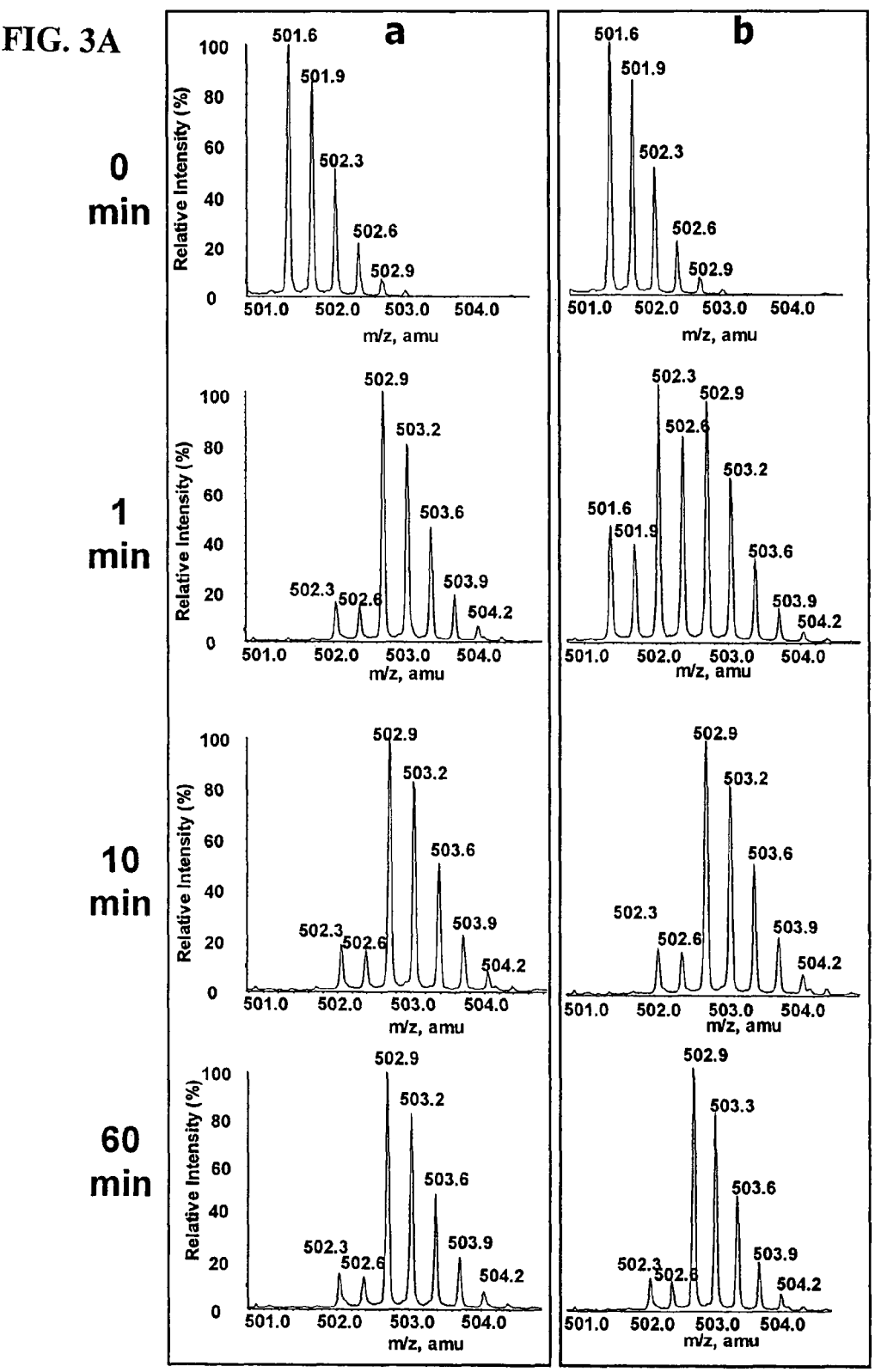
FIGS. 3A and 3B depict the mass spectra of a representative $^{18}$O labeled Lys-peptide catalyzed by Lys-C (column a—pH 5.0; column b—pH 9.0) and trypsin (column c—pH 6.0, column d—pH 8.0) at different times.
Figure 3B:
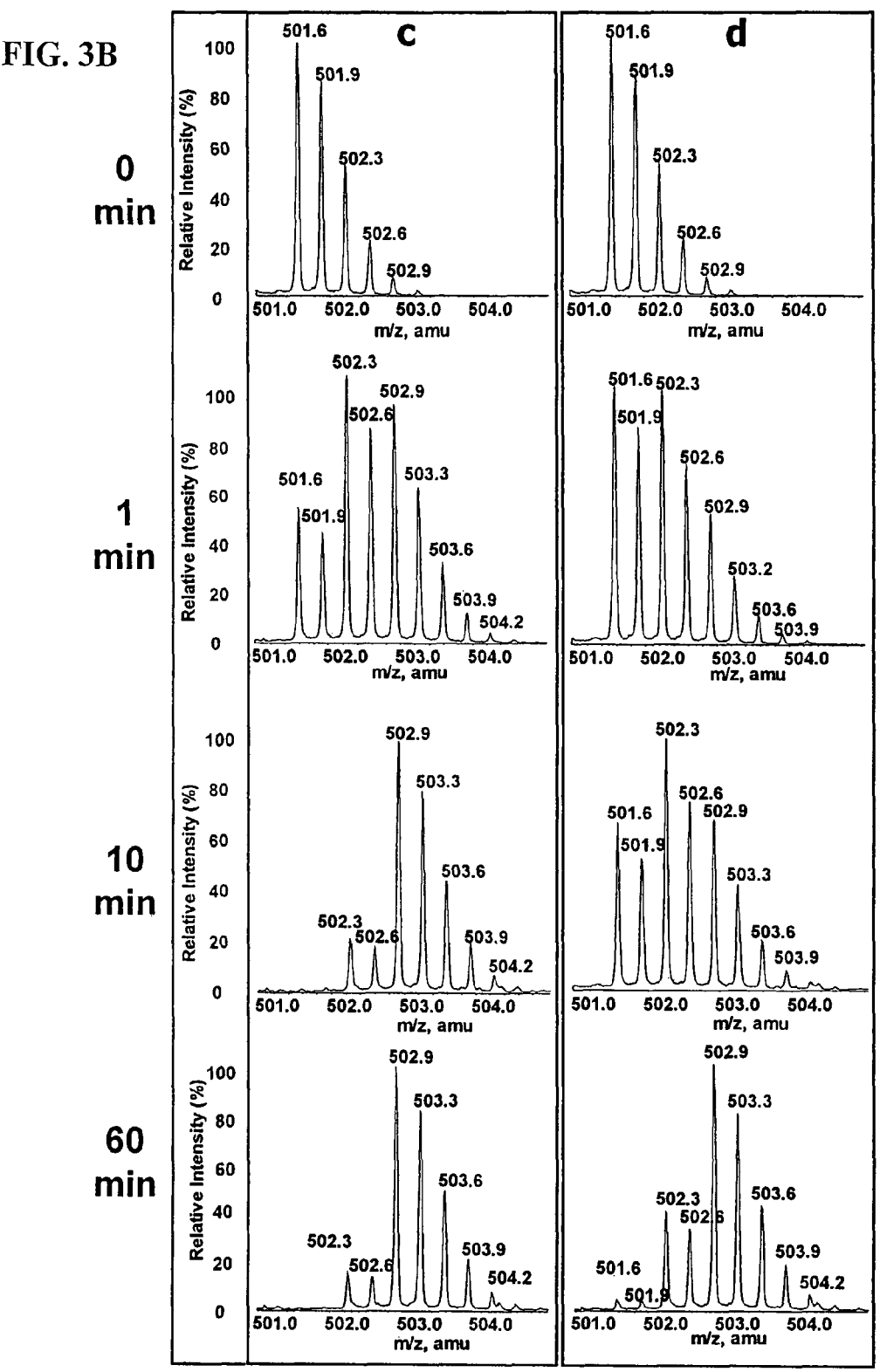

Lys-C and tryptic digests of apomyoglobin prepared in $H_2^{16}O$ solvent were incubated with Lys-C and trypsin in $H_2^{18}O$ solvent at the favorable pHs of the carboxyl oxygen exchange and amidase reactions for various reaction times. The resulting $^{18}$O labeled peptides were analyzed by LC/MS. FIGS. 3A and 3B show the mass spectra of a representative $^{18}$O-labelled apomyoglobin peptide that has a lysine residue at the C-terminus (Lys-peptide). The Lys-C results clearly show that there was complete incorporation of two $^{18}$O atoms (m/z 502.9) within 1 minute of incubation at pH 5.0 (FIG. 3A, column a), while the dominant result at pH 9.0 was the incorporation of only one $^{18}$O atom (m/z 502.3) (FIG. 3A, column b). In the case of trypsin, complete incorporation of two $^{18}$O atoms was achieved within 10 minutes of incubation at pH 6.0 (FIG. 3B, column c), while the dominant result at pH 8.0 was the incorporation of only one $^{18}$O atom, and complete incorporation of two $^{18}$O atoms was not achieved even after 60 minutes of incubation (FIG. 3B, column d). All the other Lys-peptides tested showed similar results. Note that a small fraction of one $^{18}$O atom incorporated peak (m/z 502.3) exists even after achieving complete incorporation of two $^{18}$O atoms because of the purity of $H_2^{18}O$ solvent (95% $H_2^{18}O$ and 5% $H_2^{16}O$) used in the experiments.

These results demonstrate that the enhanced rate of carboxyl oxygen exchange reaction by Lys-C and trypsin at acidic pH for Ac-Lys-OH can be generalized to peptide substrates. They also show that the carboxyl oxygen exchange activity of Lys-C for peptide substrates is significantly higher than that of trypsin, consistent with the results obtained in the Ac-Lys-OH experiments.

Figure 4:
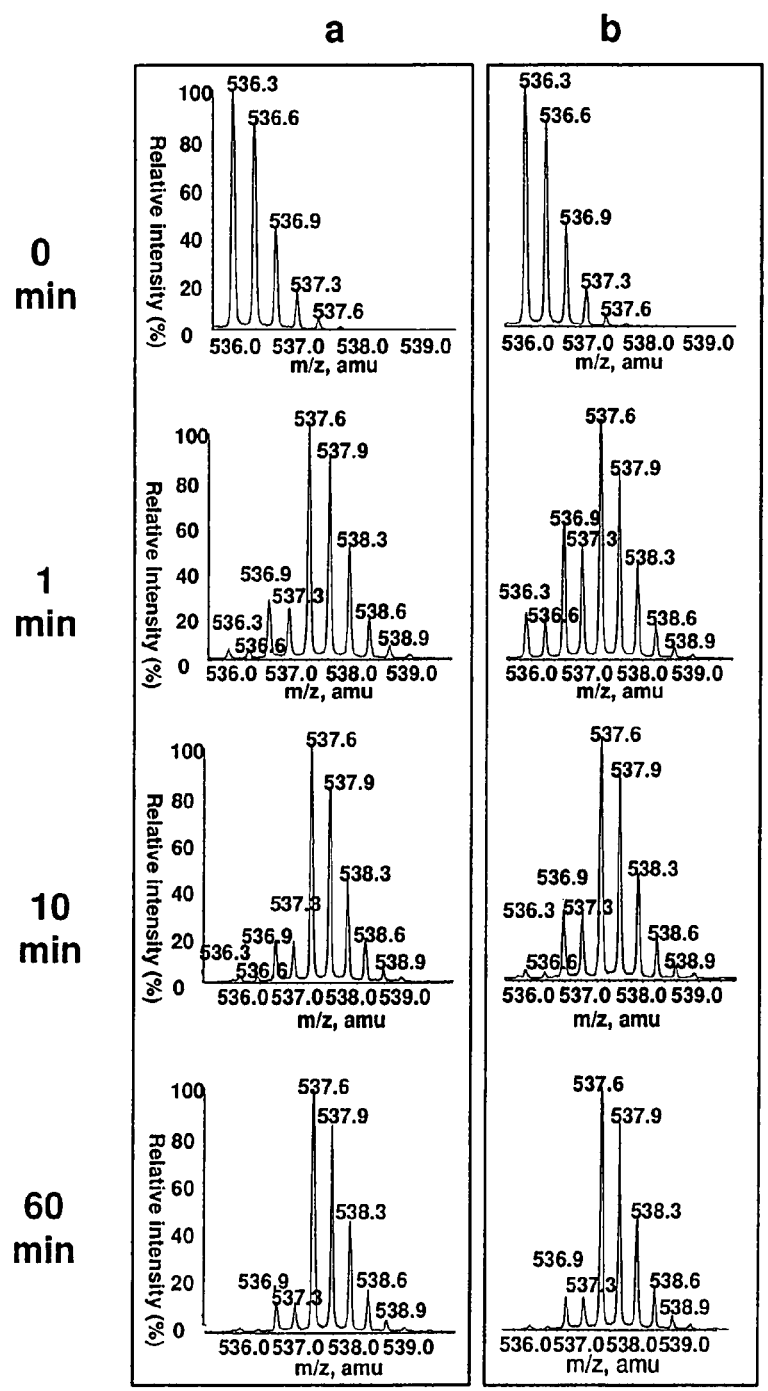
FIG. 4 depicts mass spectra of a representative $^{18}$O labeled Arg-peptide catalyzed by trypsin (a—pH 6.0, b—pH 8.0).

FIG. 4 shows the mass spectra of a representative $^{18}$O-labelled peptide that has an arginine residue at the C-terminus (Arg-peptide), which was also labeled by trypsin as described above. Complete incorporation of two $^{18}$O atoms (m/z 537.6)

was achieved within 10 minutes of incubation at pH 6.0 (FIG. 4a), while it took 60 minutes at pH 8.0 (FIG. 4b), showing that the higher carboxyl oxygen exchange rate at the acidic pH found for Lys-peptides can be expanded to Arg-peptides.

It is noticeable that the rate of $^{18}O$ atom incorporation into the Arg-peptide by trypsin is obviously faster than the rate into the Lys-peptide (FIG. 4a and b for Arg-peptide and FIG. 3B, columns c and d for Lys-peptide). After 1 minute of incubation, the dominant peak is the two $^{18}O$ atoms (m/z 537.6) incorporated peak at both pH 6.0 and 8.0 for the Arg-peptide (FIG. 4a and b), while the dominant result for Lys-peptide was the incorporation of only one $^{18}O$ atom (m/z 502.3) (FIG. 3B, columns c and d). All the other Arg-peptides derived from apomyoglobin tested showed faster $^{18}O$ atom incorporation rates than Lys-peptides.

Other Embodiments

The description of the specific embodiments of the invention is presented for the purpose of illustration. It is not intended to be exhaustive nor to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications and publications referenced herein are hereby incorporated by reference.

Other embodiments are within the claims. Although the present invention has been described with reference to preferred embodiments, workers skilled in the art will recognize that changes may be made in form and detail without departing from the spirit and scope of the invention.

The invention claimed is:

1. A method for incorporating two labeled oxygen atoms into a digested peptide comprising the steps of:
    forming a first solution of a first peptidase and $H_2^{16}O$ water;
    digesting a protein into peptides with the first solution of the first peptidase and $H_2^{16}O$ water; and
    incubating the digested peptides with a second solution of a second peptidase selected from the group consisting of Lys-C and trypsin and $H_2^{18}O$ water, the second solution having a pH within 1 pH unit of a pH which provides a maximum initial rate of reaction for carboxyl oxygen exchange for the digested peptides catalyzed by the second peptidase, for a period sufficient to incorporate two labeled oxygen atoms into at least 90% of the digested peptides.

2. The method of claim 1, wherein the second solution of the second peptidase and $H_2^{18}O$ water further comprises a buffer to maintain the pH of the second solution within 1 pH unit of the pH which provides the maximum initial rate of reaction for carboxyl oxygen exchange for the digested peptides catalyzed by the second peptidase.

3. The method of claim 1, wherein the first solution of peptidase and $H_2^{16}O$ water further comprises a buffer.

4. The method of claim 1, wherein the $H_2^{18}O$ water contains at least 95% $^{18}O$.

5. The method of claim 1, wherein two labeled oxygen atoms are incorporated into at least 99% of the digested peptides within 60 minutes.

6. The method of claim 1, wherein two labeled oxygen atoms are incorporated into at least 95% of the digested peptides within 60 minutes.

7. The method of claim 1, wherein two labeled oxygen atoms are incorporated into at least 90% of the digested peptides within 60 minutes.

8. The method of claim 1, wherein two labeled oxygen atoms are incorporated into at least 80% of the digested peptides within 60 minutes.

9. The method of claim 1, wherein the first peptidase is selected from a group consisting of an exopeptidase (EC 3.4.11-19) and an endopeptidase (EC 3.4.21-25 and 99).

10. The method of claim 9, wherein the exopeptidase is selected from a group consisting of aminopeptidase (EC 3.4.11), dipeptidyl-peptidase (EC 3.4.14), tripeptidyl-peptidase(EC 3.4.14), carboxypeptidase (EC 3.4.16-18), peptidyl-dipeptidase (EC 3.4.15), dipeptidases (EC 3.4.13), omega peptidases (EC 3.4.19), and combinations thereof.

11. The method of claim 9, wherein the endopeptidase is selected from a group consisting of serine endopeptidases (EC 3.4.21), cysteine endopeptidases (EC 3.4.22), aspartic endopeptidases (EC 3.4.23), metalloendopeptidases (EC 3.4.24), threonine endopeptidases (EC 3.4.25), unassigned endopeptidases (EC 3.4.99), and combinations thereof.

12. The method of claim 11, wherein the metalloendopeptidase is selected from a group consisting of peptidyl-Lys metallopeptidase (EC 3.4.24.20), peptidyl-Asp metallopeptidase (EC 3.4.24.33), thermolysin (EC 3.4.24.27), mycolysin (EC 3.4.24.31), and combinations thereof.

13. A method for incorporating two labeled oxygen atoms into a peptide, the method comprising:
    forming a solution of a peptidase selected from the group consisting of Lys-C and trypsin and $H_2^{18}O$ water;
    digesting a protein into peptides and incubating the peptides with the solution of peptidase and $H_2^{18}O$ water at a pH within 1 pH unit of a pH where an initial rate of reaction for carboxyl oxygen exchange for the peptides catalyzed by the peptidase is equal to an initial rate of amide hydrolysis for the peptides catalyzed by the peptidase to incorporate two $^{18}O$ atoms into at least 90% of the digested peptides.

14. The method of claim 13, wherein the solution of peptidase and $H_2^{18}O$ water further comprises a buffer to maintain the pH of the solution to within 1 pH unit of the pH where an initial rate of reaction for carboxyl oxygen exchange for the peptides catalyzed by the peptidase is equal to an initial rate of amide hydrolysis for the peptides catalyzed by the peptidase.

15. The method of claim 13, wherein digesting the protein into peptides and incubating the peptides occur contemporaneously.

16. The method of claim 13, wherein the $H_2^{18}O$ water contains at least 95% $^{18}O$.

17. The method of claim 13, wherein two labeled oxygen atoms are incorporated into at least 99% of the digested peptides within 60 minutes.

18. The method of claim 13, wherein two labeled oxygen atoms are incorporated into at least 95% of the digested peptides within 60 minutes.

19. The method of claim 13, wherein two labeled oxygen atoms are incorporated into at least 90% of the digested peptides within 60 minutes.

20. The method of claim 13, wherein two labeled oxygen atoms are incorporated into at least 80% of the digested peptides within 60 minutes.

21. A method for comparing proteins under different biological conditions using mass spectrometry, the method comprising:
    digesting a protein of first biological condition into peptides of first biological condition;

incubating the digested peptides of first biological condition with a solution of a peptidase selected from the group consisting of Lys-C and trypsin and $H_2^{18}O$ water at a pH within 1 pH unit of a pH providing a maximum initial rate of reaction for carboxyl oxygen exchange for the digested peptides catalyzed by the peptidase to incorporate two $^{18}O$ atoms into at least 90% of the digested peptides;

digesting a protein of second biological condition into peptides of second biological condition;

incubating the digested peptides of second biological condition with a solution of the peptidase and $H_2^{16}O$ water to incorporate two $^{16}O$ atoms into the digested peptides;

mixing the digested peptides of first biological condition containing $^{18}O$ and the digested peptides of second biological condition containing $^{16}O$;

performing mass spectrometry analysis of a relative ratio of $^{18}O$ and $^{16}O$ in the mixed digested peptides; and determining a ratio of labeled peptides to unlabeled peptides, wherein the ratio determined indicates a change in an amount of the protein of second biological condition relative to an amount of the protein of first biological condition.

22. The method of claim 21, wherein the solutions of peptidase and water further comprise a buffer.

23. The method of claim 21, wherein digesting the protein of first biological condition and incubating the digested peptides of first biological condition occurs contemporaneously.

24. The method of claim 21, wherein results of the mass spectrometry analysis identify at least one of a disease, symptom, mutation or biological condition in an animal.

25. A method for incorporating two labeled oxygen atoms into a peptide, the method comprising:

determining a pH that provides a maximum initial rate of reaction for carboxyl oxygen exchange for a protein catalyzed by a peptidase selected from the group consisting of Lys-C and trypsin;

digesting the protein into peptides; and incubating the peptides with a solution of the peptidase and $H_2^{18}O$ water at a pH within 1 pH unit of the pH providing the maximum initial rate of reaction for carboxyl oxygen exchange for the peptides catalyzed by the peptidase to incorporate two $^{18}O$ atoms into at least 90% of the digested peptides.

* * * * *